United States Patent [19]

MacCoss

[11] Patent Number: 4,471,113
[45] Date of Patent: Sep. 11, 1984

[54] PRODRUGS BASED ON PHOSPHOLIPID-NUCLEOSIDE CONJUGATES

[75] Inventor: Malcolm MacCoss, Naperville, Ill.

[73] Assignee: The United States of America as represented by the Department of Energy, Washington, D.C.

[21] Appl. No.: 345,442

[22] Filed: Feb. 3, 1982

[51] Int. Cl.³ .................... C07H 15/12; C07H 17/00
[52] U.S. Cl. .................................................. 536/29
[58] Field of Search ........................................ 536/29

[56] References Cited

U.S. PATENT DOCUMENTS 4,096,324  6/1978  Kelly et al. ........................ 536/29
4,291,024  9/1981  Turcotte ............................. 536/29

OTHER PUBLICATIONS

MacCoss et al., "Synthesis and Biological Activity of Novel Nucleoside–Phospholipid Prodrugs", Proced. 4th Int. Round Table, Nucleosides, Nucleotides and their Biol. Appl'ns Antwerp, 4–6, Feb., 1981, pp. 46–47.
Matsushita et al., Cancer Research 41, 2707–13, Jul. 1981.
MacCoss et al., Biochem. & Biophys. Res. Comm. 85 (2), Nov. 29, 1978, pp. 714–723.
Turcotte et al., Biochemica et Biophysica Acta, 619 (1980), pp. 604–618.

Primary Examiner—Ethel G. Love
Attorney, Agent, or Firm—William Lohff; Robert J. Fisher; Michael F. Esposito

[57] ABSTRACT

The invention relates to the production of a single diastereomeric form of a phospholipid araC conjugate as a prodrug.

5 Claims, No Drawings

PRODRUGS BASED ON PHOSPHOLIPID-NUCLEOSIDE CONJUGATES

CONTRACTUAL ORIGIN OF THE INVENTION

The United States Government has rights in this invention pursuant to Contract No. W-31-109-ENG-38 between the U.S. Department of Energy and Argonne National Laboratory.

BACKGROUND OF THE INVENTION

The drug 1-β-D-arabinofuranosylcytosine (araC) is a nucleoside analog which has proven useful as a chemotherapeutic agent in the clinical treatment of certain types of cancer. It has also been used as an antiviral agent. In a similar manner, the drug 9-β-D-arabinofuranosyladenine (araA) has been found useful. A third drug, 4-amino-7H-pyrrolo[2,3-d]pyrimidine (tubercidin), although exhibiting high toxicity in many instances, has been shown to be extremely effective in the treatment of basal skin carcinoma when the drug is localized topically on the lesion.

There are several problems in chemotherapy with the arabinonucleosides araC and araA. The first is their rapid catabolism via deaminase enzymes to ineffective metabolites. In the case of araC, high levels of deoxycytidine deaminase exist in the liver of humans, and the ineffective metabolite 1-β-D-arabinofuranosyluracial (araU) appears rapidly in human urine after injection of araC. Due to this degradation, the half-life of araC in humans has been estimated to be only 3 to 9 minutes. The second problem is the eventual resistance developed by the cells. In experimental tumor systems, this resistance has been attributed to the selection of cells in which the deoxynucleoside kinases have a low specific activity compared to the wild type, so that the arabinoside is not metabolized to the 5'-triphosphate, the actual cytotoxic metabolite. A third problem is the toxicity of the arabinonucleosides in rapidly dividing normal tissue as well as against neoplastic cell types.

One approach to circumvent these drawbacks involves the attachment of drugs to a nontoxic "carrier molecule" that protects the drug from degradation. Subsequently, the drug is released by enzymatic or chemical action. A particular example utilizes lipophilic fatty acid esters such as 5'-O-adamantoyl-araC, 5'-O-palmitoyl-araC, and 5'-O-valeryl-araA as molecular depots or target "prodrugs" of the parent arabinonucleoside. Such derivatives protected the parent drug from catabolic degradation, however, in vivo studies have indicated no therapeutic advantages of 5'-O-palmitoyl-araC, presumably due to poor drug absorption. Recently, there has been some indication of improved efficacy, relative to araC, of corticosteroid-araC conjugates and promising preliminary antitumor data have been reported.

Since the effectiveness of the enzymes which act to release a particular drug from a prodrug is influenced by the particular carrier, it is of interest to provide prodrugs with different carriers. It is also of interest to provide prodrugs based on a mixture of different carriers. However, it is not always possible to prepare new prodrugs utilizing known techniques and it becomes necessary to develop new methods to achieve the desired compounds in reasonably pure form.

Accordingly, one object of this invention is the preparation and use of new prodrugs based on phospholipid-drug conjugates. A second object of the invention is the preparation and use of prodrugs based on different phospholipid carriers. A third object of the invention is to prepare such phospholipid-drug conjugates with different types of linkages between the phospholipid moiety and the drug. Another object of the invention is the development of a method for preparing new prodrugs. Yet another object of the invention is related to new compositions of matter useful as prodrugs. An additional object is the preparation of new prodrugs in pure form. A further object is the preparation of phospholipid-drug conjugates as new prodrugs in which the phospholipid moiety exists as a single optical isomer, namely that which is commonly found in nature, the L form. Such single diastereomers are likely to be the preferred substrates for the enzymes responsible for release of the drug from the prodrug. These and other objects will become apparent from the following description.

SUMMARY OF THE INVENTION

Briefly, the invention relates to a process for producing a single diastereomeric form of a phospholipid-araC conjugate in which the drug araC is covalently attached to a phospholipid via a monophosphate linkage in substantially pure form by procedures involving the selective blocking of the 2'- and 3'-hydroxyl functions and the exocyclic —NH₂ function on the nucleoside moiety to avoid the production of isomers. The process provides a means of producing a class of new prodrugs identified

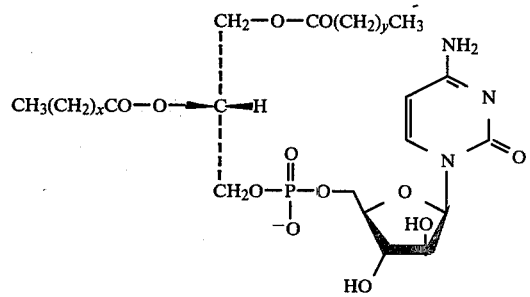

where x and y are integers from 12–16. In some instances, the monophosphate-linked derivatives have limited solubility in saline solution and mixtures of conjugates having monophosphate and diphosphate linkages are shown to be useful in providing prodrug mixtures which exhibit the desired solubility and offer different properties. In addition, the invention provides new compositions identified as araCDP-L-distearin, araCDP-L-dimyristin, araCDP-L-diolein, dipalmitin, araADP-L-dipalmitin, and tubercidin-L-dipalmitin.

The invention also provides for mixtures of the above mentioned monophosphate-linked derivatives with diphosphate-linked derivatives, bearing the same drug (araC) and for mixtures bearing different drugs (araA and araC) attached by mono- or diphosphate linkages to different phospholipid carriers.

DETAILED DESCRIPTION OF THE INVENTION

In the inventive process or method, the drug araC identified by the formula

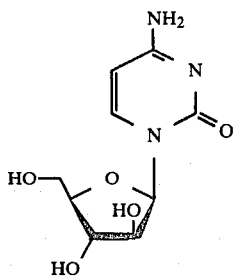

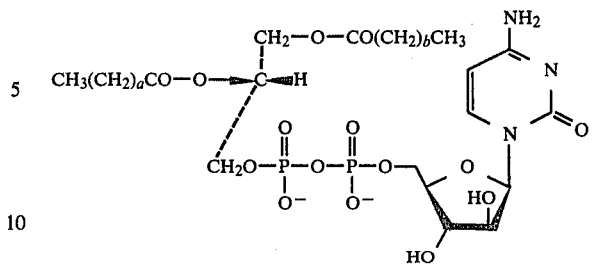

is reacted with t-butyldimethylsilyl chloride to provide selective protection of the 5'-hydroxyl group of the araC. Acylation of the resulting 5'-O-TBDMS-araC (where TBDMS represents the t-butyldimethylsilyl group) is carried out with levulinic anhydride (generated in situ) to produce fully blocked 5'-O-TBDMS-2',3',N⁴-triLv-araC, where Lv represents the levulinyl group. Selective removal of the 5'-TBDMS group is achieved using tetrabutylammonium fluoride (TBAF)-/acetic acid in tetrahydrofuran (THF). The 2',3'-N⁴-trilevulinyl-araC so obtained is condensed with L-α-dipalmitoylphosphatidic acid (pyridinium salt). It should be noted that several other blocking groups were tried for this nucleoside, but were ultimately rejected in favor of the levulinyl group due to intolerable amounts of degradation during the deblocking steps. The fully blocked product so obtained was not isolated but treated with pyridine/water and then hydrazine in pyridine/acetic acid to produce the diastereomeric N-phosphoryl dicyclohexylurea adduct of araCMP-L-dipalmitin. The structure was identified by elemental analysis and by NMR, IR, and UV spectroscopy. The final product, araCMP-L-dipalmitin, was obtaind by hydrolysis of the N-phosphoryl dicyclohexylurea adduct with CHCl$_3$-CH$_3$OH-water (2:3:1 by weight) at 60° C. for 2 hours. After work-up, the product was the sodium salt of araCMP-L-dipalmitin in a yield of about 65–90%, based on the N-phosphoryldicyclohexylurea adduct.

Accordingly, the method provides a class of monophosphate-linked derivatives as prodrugs identified by the formula:

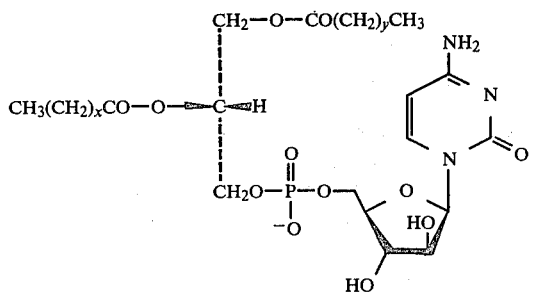

where x and y are integers from 12–16. Further, the invention relates to mixtures of the above monophosphate-linked and the diphosphate-linked derivatives identified below by the formula where a and b are integers from 12–16. By use of these mixtures, prodrugs with a combination of properties with respect to enzymes may be provided. In addition, these mixtures provide a means for solubilizing some of the monophosphate-linked derivatives. Ratios are in the order of 1:2 to 3:1 by weight.

Another contribution of the invention involves the new compositions araCDP-L-distearin, araCDP-L-dimyristin, araCDP-L-diolein (an example of a diphosphate-linked derivative bearing unsaturation in the fatty acid acyl side chains), araADP-L-dipalmitin, and tubercidin-L-dipalmitin. Although the corresponding araCDP-L-dipalmitin is known, the changes in fatty acid chain length provides valuable new compounds in which the dose required for 50% inhibition of growth of cells in tissue culture (ED$_{50}$) varies with chain length. For the araCDP-L-dimyristin, in mouse myeloma MPC-11 (subclone 66.2) cells the ED$_{50}$ is 15 μM, while for araCDP-L-dipalmitin, the ED$_{50}$ is 65 μM and for araCDP-L-distearin, the ED$_{50}$ is 195 μM. For araCDP-L-diolein, the ED$_{50}$ is 62 μM.

The following examples are provided for illustration purposes and are not intended to be construed as limiting the invention.

EXAMPLE I (a) In the preparation of araCMP-L-dipalmitin from araC, the first intermediate to be prepared was 5'-O-t-butyl dimethylsilyl-1-β-D-arabinofuranosylcytosine.

To a solution of araC (2.0 g, 0.0082 mol) and imidazole (1,237 g, 0181 mol) in dry N,N-dimethylformamide (DMF) was added tert-butyldimethylsilyl chloride (1.363 g, 0.00904 mol), and the solution was stirred at room temperature in a desiccator overnight. The reaction mixture was evaporated to dryness in vacuo (one additional time from toluene) and water (150 mL) was added to the residue. After trituration a white powder was formed which was filtered off and washed with water to yield 4.8 g of crude product. This was recrystallized from ethyl acetate (ca. 200 ml) containing a little MeOH (solution was cooled to 5° C. before filtering) to give 2.48 g (84.5%) of the product. The product was homogenous by TLC (Eastman silica gel plates) using the upper phase of ethyl acetate-n-propanal-H$_2$O (4:1:2), NMR and UV spectroscopy, was pure as the monohydrate by elemental analysis for C, H, and N, and had mp 230°–231° C.

(b) The second intermediate to be prepared was 5'-O-t-butyldimethylsilyl-2',3',N⁴-trilevulinyl-1-β-D-arabinofuranosylcytosine.

Levulinic acid (1.04 mL) was dissolved in dry ethyl acetate (25 mL) and N,N'-dicyclohexylcarbodiimide, DCC, (2.1 g, 0.01 mol) was added. The reaction mixture was shaken occasionally while being stored in a desiccator at room temperature to 1.5 hr. The mixture was then filtered directly onto a suspension of the product formed in Example 1a (0.4 g, 0.00112 mol) and N,N-dimethylaminopyrimidine (0.16 g, 0.0013 mol) in dry ethyl acetate (25 mL), washing the filter pad, N,N'-dicyclohexylurea, DCU, with more dry ethyl acetate (25 mL). This reaction was stirred at room temperature for 4.5 hr when dry EtOH (4 mL) was added. After an additional 30 min, the precipitate (DCU) was filtered off and the filtrate was extracted with ice-cold saturated NaHCO$_3$ solution (3×50 mL) and then water (3×50 mL) before being evaporated to dryness. The residue was dissolved in a minimum volume of CHCl$_3$ and applied to a column of silica gel (55×3 cm, wet packed in CHCl$_3$). The column was developed with CHCl$_3$ (1.2 L) and then with 5% MeOH in CHCl$_3$. Fractions containing the required product were pooled and evaporated to dryness to give 0.713 g (97.8%) of the product, which was homogeneous (Rf 0.63) by TLC (Merck silica gel plates) using EtOH-CHCl$_3$ (1:9) as developer and by NMR, and was used directly in the next preparation.

(c) The third intermediate to be prepared was 2',3',N$^4$-trilevulinyl-1-β-D-arabinofuranosylcytosine.

The product of Example 1(b) prepared above (0.713 g, 0.0011 mol) was dissolved in a premade solution of 1M tetrabutylammonium fluoride (TBAF) in tetrahydrofuran (THF) (5 mL) containing glacial acetic acid (0.5 mL). The reaction mixture was left at room temperature for 1.5 hr and was then evaporated to dryness in vacuo (one additional time from toluene). TLC (Merck silica gel plates) using MeOH-CHCl$_3$ (1:9) as developer indicated almost complete reaction and the residue was dissolved in a minimum amount of CHCl$_3$ and applied to a silica gel column (43×3 cm), wet-packed on CHCl$_3$. The column was developed successively with CHCl$_3$ (300 mL), 5% MeOH in CHCl$_3$ (350 mL), and then 8% MeOH in CHCl$_3$ (400 mL). Fractions containing the required product were pooled and evaporated to dryness, yielding a clear gum. Crystallization from acetone-CCl$_4$ gave 0.433 g (74%) of the analytically pure (C,H,N) product which was homogenous by TLC and NMR spectroscopy, and had mp 142°-144°.

(d) Prior to the preparation of the fourth intermediate, the pyridinium salt of L-α-dipalmitoyl phosphatidic acid was prepared. In the preparation, commercially available L-α-dipalmitoylphosphatidic acid, disodium salt (1.0 g, 0.00149 mol) was dissolved in 250 mL of CHCl$_3$-MeOH-pyridine-H$_2$O (3:3:1:1) and applied to a column of Dowex 50W×8 (pyridinium) resin. The required product was eluted with the solvent front and the solution was evaporated to dryness [coevaporated several times from CHCl$_3$-MeOH (1:1)]. The residue was triturated with acetone and the white solid was filtered off, washed with acetone, and dried over P$_2$O$_5$ in vacuo for 24 hr.

(e) The fourth intermediate to be prepared was 1-α-D-arabinofuranosylcytosine 5'-monophosphate-L-1,2-dipalmitin-N-phosphoryl dicyclohexylurea adduct. In the preparation, a mixture of the compound from Example 1(c) (0.270 g, 0.0005 mol) and L-α-dipalmitoylphosphatidic acid, pyridinium salt (0.356 g, 0.00051 mol) was dissolved in dry pyridine and the mixture was rendered anhydrous by repeated evaporation from dry pyridine in vacuo. After addition of DCC (0.65 g, 0.00315 mol) the mixture was again evaporated to dryness in vacuo several times from dry pyridine. Finally, the volume was reduced to ca. 2 mL and the mixture was left at room temperature in a desiccator for 4 days. Ice (ca. 2 g) was then added and the mixture was allowed to stand at room temperature overnight. The mixture was extracted with petroleum ether (30–60; 3×5 mL) and then evaporated to dryness in vacuo. Pyridine was removed by several coevaporations in vacuo from toluene. The residue was dissolved in CHCl$_3$-MeOH (1:1, 5 mL) was stored at 4° overnight. The white precipitate of DCU so formed was filtered off and washed with the same solvent (2×2 mL). Combined filtrate and washings were evaporated to dryness and the residue was dissolved in CHCl$_3$ and applied to a column (30×2.5 cm) of silica gel wet-packed in CHCl$_3$. The column was developed with CHCl$_3$ and then 2% MeOH in CHCl$_3$ and fractions containing the major uv-absorbing product were pooled and evaporated to dryness. The residue was dissolved in 2 mL of pyridine-acetic acid (4:1) and hydrazine hydrate (0.1 mL) was added. After stirring for 2 hr, TLC (Merck silica gel plates; CHCl$_3$-MeOH-H$_2$O, 65:25:3 as developer) showed that deblocking of the levulinyl groups was complete and so the reaction mixture was evaporated to dryness. The residue was dissolved in CHCl$_3$ (30 mL) and applied to a column of silica gel which was developed with 2% MeOH in CHCl$_3$ (500 mL) and then 10% MeOH in CHCl$_3$. Fractions containing the required product were pooled and evaporated to small volume and then MeOH was added. A white precipitate formed which was filtered off and dried in vacuo over P$_2$O$_5$. The yield was 0.120 g (22%) and the diastereomeric mixture of the product so formed had mp 101°-103°. TLC (Merck silica gel plates developed in CHCl$_3$-MeOH-H$_2$O, 65:25:3) showed one UV-absorbing spot which was also positive using a phosphate spray reagent. IR (KBr, disc) showed 1753, 1700 cm$^{-1}$ (C=O), 1255 cm$^{-1}$ (P=O), 1168 cm$^{-1}$ (P=N), and 1045, 1020 cm$^{-1}$ (P-O-C) as identified bands. Further characterization of the product was obtained from $^{31}$P and $^1$H NMR spectroscopy, and from the elemental analysis (C,H,N,P) of the monohydrate.

(f) In the preparation of the sodium salt of araCMP-L-dipalmitin, a solution of the product from Example 1(e) (0.165 g, 0.00015 mol) in CHCl$_3$-MeOH-H$_2$O (2:3:1; 50 mL) was heated at 60° for 2 hr. Other methods of carrying out this step include: (i) butanol-acetic acid-H$_2$O (5:2:3) at room temperature for 3 days. (ii) 10M H$_2$O in pyridine at room temperature for 4 days, or (iii) CHCl$_3$-MeOH-H$_2$O (2:3:1). Monitoring by TLC (Merck silica gel plates developed in MeOH-CHCl$_3$, 3:7) indicated complete reaction and the solution was evaporated to dryness. The residue was dissolved in CHCl$_3$-MeOH-H$_2$O (4:6:1; 100 mL) and applied to a column of DEAE-Sephadex (acetate form; 15×4 cm) packed in the same solvent. Elution was initially with CHCl$_3$-MeOH-H$_2$O (4:6:1; 500 mL) and then with a linear gradient (700 mL in each reservoir) of 0-0.1N ammonium acetate made up in CHCl$_3$-MeOH-H$_2$O (4:6:1). Fractions containing the required product were pooled and evaporated to small volume. Acetone (50 mL) was added and the white precipitate of the NH$_4$$^+$ salt so obtained was filtered off and then converted to the Na$^+$ salt by dissolution in CHCl$_3$-MeOH-H$_2$O (4:6:1) and passage down a Cellex-CM (Na$^+$ form) column 31×2.5 cm), packed, and developed in the same solvent. The fractions containing the required product was pooled and concentrated, and the material was obtained as a white precipitate upon addition of acetone-H$_2$O (9:1). This material was filtered off, washed with acetone and dried over P$_2$O$_5$ in vacuo for 20 hr. Yield 0.122 g (89%); mp 212°-214° (decomp.). The product so obtained was homogeneous by TLC, $^{31}P$ and $^1H$ NMR spectroscopy, and was pure as a monohydrate by elemental analysis (C,H,N,P).

EXAMPLE II

In the preparation of araCDP-L-dimyristin

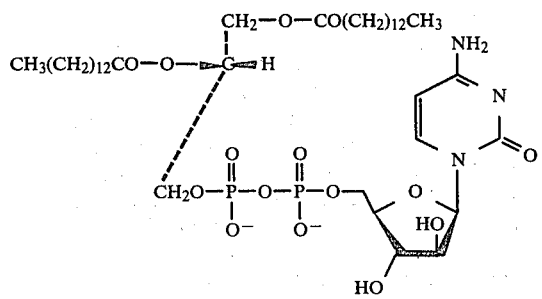

The commercially available L-α-dimyristoylphosphatidyl choline (0.500 g; 0.0072 mol) was suspended in 30 mL of 0.2M NaAc/HOAc buffer, pH 5.45 containing 0.04M CaCl$_2$. This material was subjected to sonication (Biosonik III) for 30 min. To this mixture was added 0.014M sodium dodecyl sulfate solution (15 mL) and Et$_2$O (10 mL) and the total was added to a solution of phospholipase-D (100 mg) in 50 mL of the above-mentioned 0.2M NaOAc/HoAc buffer containing 0.04M CaCl$_2$, the reaction vessel being a screw-top plastic container. The mixture was incubated at 30° and monitored by TLC (Merck silica gel plates using CHCl$_3$-MeOH-H$_2$O-HOAc, 25:15:4:2 as developer). After 22 hr and again after 96 hr additional 20 mg increments of phospholipase-D were added. After 10 days the reaction was acidified to pH 1-1.5 with conc. HCl and extracted with 100 mL of CHCl$_3$-MeOH (1:1) and then with CHCl$_3$ (100 mL). The combined organic layers were evaporated to dryness to yield 0.45 g of a white solid (TLC showed the major spot to be L-α-dimyristoylphosphatidic acid slightly contaminated with trace amounts of the starting material and one other unidentified compound). This material was mixed with the known 1-β-D-arabinofuranosylcytosine 5'-monophosphomorpholidate, 4-morpholine-N,N'-dicyclohexylcarboxamidinium salt (0.48 g; 0.0007 mol) and dissolved in dry pyridine (20 mL). The solution was evaporated to dryness in vacuo 5 times from dry pyridine and then was concentrated to 15 mL from 50 mL of dry pyridine. This solution was stoppered and stored in a desiccator for 4 days with occasional shaking. The reaction mixture was then evaporated to dryness in vacuo and the residue was co-evaporated from toluene (4×20 mL). This residue was then dissolved in 30 mL of CHCl$_3$-MeOH-H$_2$O (2:3:1) and acidified to pH 3 with 0.1N HCl. Two layers formed and the aqueous layer was washed with CHCl$_3$ (2×15 mL). The combined organic layers were evaporated to dryness and the residue was dissolved in CHCl$_3$-MeOH-H$_2$O (2:3:1) and applied to a DEAE-Sephadex (acetate form) column (3.25×52 cm) packed in the same solvent. The column was eluted with 500 ml of CHCl$_3$-MeOH-H$_2$O (2:3:1) and then with a linear gradient (2 L in each reservoir) of 0-0.2M ammonium acetate made up in the same solvent. Fractions containing the required product as judged by TLC (Merck silica gel plates using CHCl$_3$-MeOH-H$_2$O-HOAc, 25:15:4:2 as developer) was pooled and evaporated to 120 mL. This mixture was extracted with CHCl$_3$ (500 mL) and the organic layer was evaporated to yield 0.325 g (50%) of the product as the diammonium salt. This material was dissolved in a minimum of CHCl$_3$-MeOH-H$_2$O (2:3:1) and converted to the disodium salt by passage down a column (2×12 cm) of Cellex-CM (Na$^+$ form) which had been packed in the same solvent mixture. The product was obtained as a tractable white precipitate by dissolution in CHCl$_3$ and addition of acetone. This was filtered off and washed well with acetone before being dried in vacuo over P$_2$O$_5$. The material had a melting behavoir in which the sample turns brown at 195°-200° with sharp melting at 209°-210°. The product was homogeneous by TLC and $^1H$ NMR spectroscopy, and was pure as the dihydrate by elemental analysis (C,H,N,P).

EXAMPLE III

1-β-D-Arabinofuranosylcytosine-5'-diphosphate-L-1,2-distearin

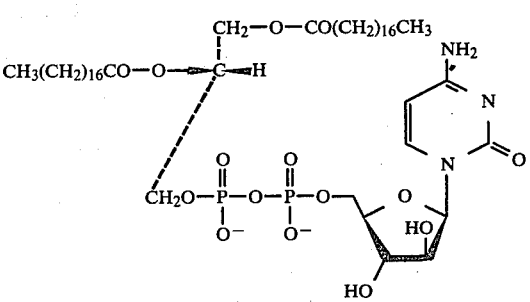

was prepared as described above for Example II starting from L-α-distearoylphosphatidyl choline to give the product in 40% yield. The material had a melting behavior in which the sample slowly turns brown above 190°, with sharp melting at 204°-205°. The product was homogeneous by TLC and $^1H$ NMR spectroscopy, and was pure as the hexahydrate by elemental analysis (C,H,N,P).

EXAMPLE IV

1-β-D-Arabinofuranosylcytosine-5'-diphosphate-L-1,2-diolein

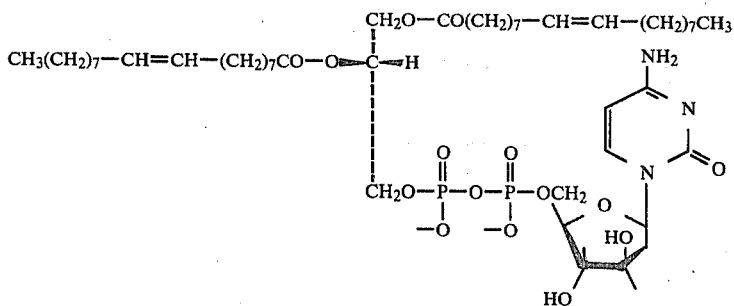

was prepared as described above for Example II starting from L-α-dioleoylphosphatidyl choline to give the product in 44% yield. The material had a melting behavior in which the sample turns brown at 180°–185°, with sharp melting at 204°–205°. The product was homogeneous by TLC and $^1$H NMR spectroscopy, and was pure as the trihydrate by elemental analysis (C,H,N,P).

EXAMPLE V

1-β-D-Arabinofuranosylcytosine-5′-diphosphate-L-1,2-di[1-$^{14}$C]palmitin was prepared as described above for Example II starting from L-α-di[1-$^{14}$C]palmitoylphosphatidyl chloine (50 μCi of 114 mCi/mmole) diluted with cold L-α-dipalmitoylphosphatidyl choline (0.043 g; 0.000057 mol). The overall yield was 30% and the final product had a specific activity of 0.68 mCi/mmole.

EXAMPLE VI

9-β-D-Arabinofuranosyladenine-5′-diphosphate-L-1,2-dipalmitin

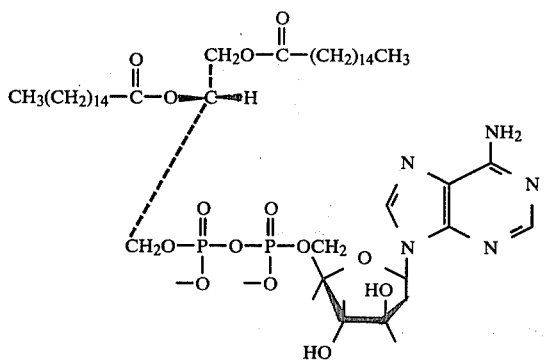

was prepared as described above for Example II starting from 9-β-D-arabinofuranosyladenine 5′-monophosphomorpholidate, 4-morpholine-N,N′-dicyclohexylcarboxamidinium salt and L-α-dipalmitoylphosphatidic acid, pyridinium salt. The product was homogeneous by TLC and $^1$H NMR spectroscopy.

EXAMPLE VII

Tubercidin-5′-diphosphate-L-1,2-dipalmitin

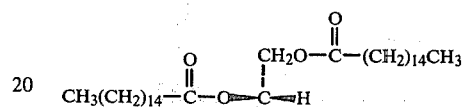

was prepared as described above for Example II starting from tubercidin 5′-monophosphomorpholidate, 4-morpholine-N,N′-dicyclohexylcarboxamidinium salt and L-α-dipalmitoylphosphatidic acid, pyridinium salt. The product was homogeneous by TLC and $^1$H NMR spectroscopy.

EXAMPLES VIII–XVI

In the study of biological activity of the compositions of Examples 1f and II–VII, it was first necessary to prepare solutions at room temperature. Suspensions of the compounds of Examples 1f and II–VII were all subjected to known sonication techniques in order to aid solubilization. Using these methods, araCDP-L-distearin remained slightly opalescent but was quantitatively (as estimated by UV) filtered through a 0.45μ Millipore filter and the filtered solution was used in in vitro studies as such. However, the araCMP-L-dipalmitin resisted solubilization even when samples were mixed with several types of detergent prior to sonication. Finally, the best means of solubilization was achieved by mixing the sample with araCDP-L-dipalmitin prior to sonication. In this fashion, mixtures having ratios (by weight) of the mono- to diphosphate linked derivatives from 1:2 through to 3:1 were made up and such mixtures were used for the in vitro inhibition studies.

In in vitro studies, the compounds of Examples 1f and II–VII were tested for antiproliferative activity against the mouse myeloma MPC-11 (subclone 66.2) cell line and the data are shown in Table I. The testing of different ratios of mono- and diphosphate linked derivatives did not markedly affect the overall ED$_{50}$ of the samples, which were also similar to that obtained for the diphosphate linked derivative alone. This indicates extremely similar antiproliferative activities of the mono- and diphosphate linked derivatives.

TABLE I

In Vitro antiproliferative activity against mouse myeloma MPC-11 cell line[a]

| Compound | $ED_{50}$[b] | $LD_{50}$[c] |
|---|---|---|
| araC | 0.99 (0.85) | 1.91 |
| araCDP—L-dipalmitin | 65 (42.1) | 68.5 |
| araCDP—L-distearin | 195 (168.5) | 164.5 |
| araCDP—L-dimyristin | 15 (13.1) | 15.2 |
| araCDP—L-diolein | 62 (43.9) | 54.8 |
| araCMP—L-dipalmitin:araCDP—L-dipalmitin | | |
| 1:2 | 138 | |
| 1:1 | 149 | |
| 2:1 | 109 | |
| 3:1 | 124 | |
| TubercidinDP—L-dipalmitin | 5.0 | |
| araADP—L-dipalmitin | Not soluble | |

[a]Values are in μM.
[b]Values listed are for samples made up in H₂O, values in parentheses are for samples made up in 0.9% saline/0.1 mM Tris, pH 7.1.
[c]Values are for samples made up in H₂O.

It is to be understood that the structural formulas for the prodrugs described and claimed herein are intended to refer to salts from the usual cations such as sodium potassium and the like, and other combinations commonly used in the medical field.

The foregoing description of embodiments of the invention has been presented for purposes of illustration and description. It is not intended to be exhaustive or to limit the invention to the precise form disclosed. Other modifications and variations are possible in light of the above teaching.

The embodiments of the invention in which an exclusive property or privilege is claimed are defined as follows:

1. A method for producing a pure diastereomer of the following phospholipid-araC conjugate

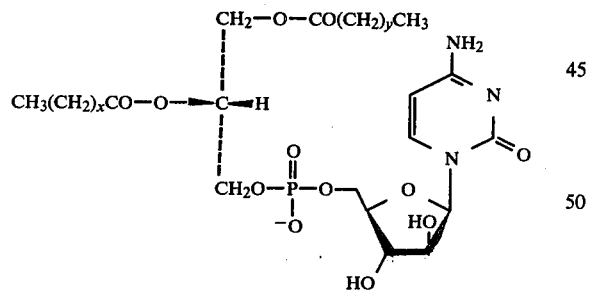

from a first compound

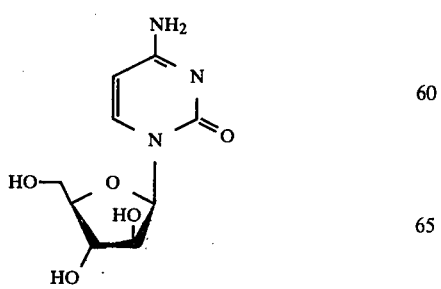

where x and y are integers from 12–16, said process comprising the steps of:

(a) reacting the first compound with t-butyldimethylsilyl chloride under silylation conditions to produce a second compound

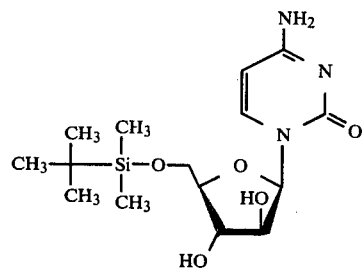

(b) reacting the second compound with levulinic anhydride under acylating conditions to produce a third compound

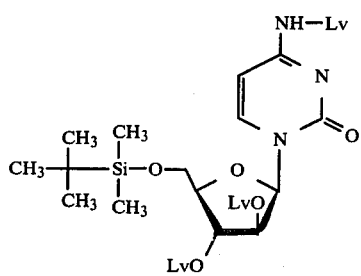

where Lv is the levulinyl group (c) deblocking the third compound to produce a fourth compound

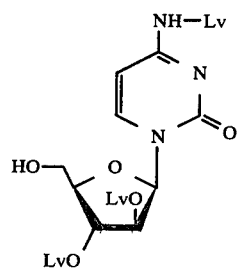

(d) condensing the fourth compound with

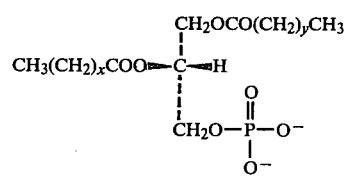

to produce a fifth compound

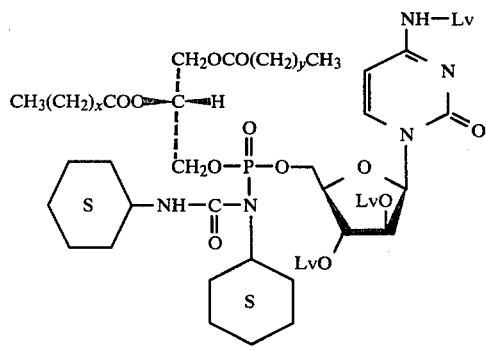

(e) deblocking the fifth compound to produce a sixth compound as a mixture of diastereomers at phosphorous:

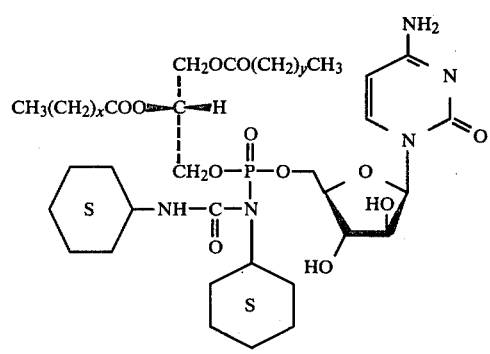

(f) and hydrolyzing the sixth compound to produce said monophosphate-linked derivative as a single diastereomer.

2. The process of claim 1 wherein x and y are equal to 14.

3. A mixture of the single diastereomer

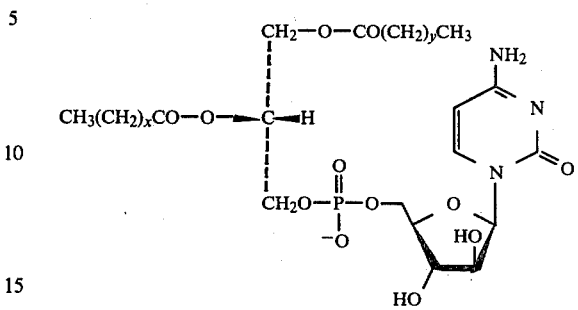

where x and y are integers from 12–16, and the single diastereomer of the following compound

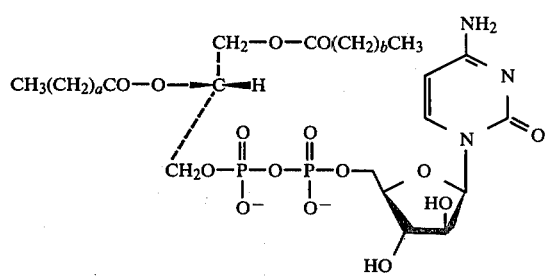

where a and b are integers from 12–16, said diastereomers being present respectively, in a weight ratio in the order of 1:2 to 3:1.

4. The mixture of claim 3 wherein x and y and a and b each equal 14.

5. The mixture of claim 3 characterized by being soluble in a saline solution.

* * * * *